(12) United States Patent
Miyazaki

(10) Patent No.: US 10,996,217 B2
(45) Date of Patent: May 4, 2021

(54) METHOD FOR EXAMINING RENAL DISEASE

(71) Applicants: SEKISUI MEDICAL CO., LTD., Tokyo (JP); Toru Miyazaki, Tokyo (JP)

(72) Inventor: Toru Miyazaki, Tokyo (JP)

(73) Assignees: SEKISUI MEDICAL CO., LTD., Tokyo (JP); Toru Miyazaki, Tokyo (JP)

( * ) Notice: Subject to any disclaimer, the term of this patent is extended or adjusted under 35 U.S.C. 154(b) by 354 days.

(21) Appl. No.: 15/749,696

(22) PCT Filed: Jun. 1, 2016

(86) PCT No.: PCT/JP2016/066227
§ 371 (c)(1),
(2) Date: Feb. 1, 2018

(87) PCT Pub. No.: WO2017/022315
PCT Pub. Date: Feb. 9, 2017

(65) Prior Publication Data
US 2018/0224437 A1 Aug. 9, 2018

(30) Foreign Application Priority Data
Aug. 6, 2015 (JP) .............................. JP2015-155975

(51) Int. Cl.
*G01N 33/53* (2006.01)
*G01N 33/543* (2006.01)
*G01N 33/68* (2006.01)

(52) U.S. Cl.
CPC ....... *G01N 33/543* (2013.01); *G01N 33/6893* (2013.01); *G01N 2333/70596* (2013.01); *G01N 2800/347* (2013.01); *G01N 2800/56* (2013.01)

(58) Field of Classification Search
None
See application file for complete search history.

(56) References Cited

U.S. PATENT DOCUMENTS

| 5,420,016 A * | 5/1995 | Boguslaski ............... C12Q 1/04 106/2 |
| 2011/0123550 A1* | 5/2011 | Shibayama ........ C07K 16/2818 424/172.1 |
| 2013/0115220 A1* | 5/2013 | Miyazaki ........... A61K 31/7088 424/145.1 |

FOREIGN PATENT DOCUMENTS

| WO | 2011/145725 A1 | 11/2011 |
| WO | 2015/119253 A1 | 8/2015 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Kai et al., Stabilization and Augmentation of Circulating AIM in Mice by Synthesized IgM-Fc, , PLOS ONE, May 2014, vol. 9, Issue 5, pp. 1-9. (Year: 2014).*
Arai et al., Obesity-Associated Autoantibody Production Requires AIM to Retain the Immunoglobulin M Immune Complex on Follicular Dendritic Cells, Cell Reports, 3, Apr. 25, 2013, pp. 1187-1198. (Year: 2013).*
Miyazaki, T. et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily", J. Exp. Med., Jan. 18, 1999, vol. 189, No. 2, pp. 413-422; cited in the Specification.
Sarrias, M-R. et al., "A Role for Human SP Alpha as a Pattern Recognition Receptor", The Journal of Biological Chemistry, Oct. 21, 2005, vol. 280, No. 42, pp. 35391-35398; cited in the Specification.
Kurokawa, J. et al., "Macrophage-Derived AIM Is Endocytosed into Adipocytes and Decreases Lipid Droplets via Inhibition of Fatty Acid Synthase Activity", Cell Metabolism, Jun. 9, 2010, pp. 479-492; cited in the Specification.
Tissot, Jd. et al., "IgM are associated to Sp Alpha (CD5 antigen-like)", Electrophoresis, 2002, pp. 1203-1206; cited in the Specification.
Miyazaki, T., "Latest Topics on Macrophage-derived Protein AIM—Their Diverse Functions and Association with Lifestyle-Related Diseases", Nippon Rinsho, 2013, vol. 71, No. 9, pp. 1681-1689; cited in the Specification.
Arai, S. et al., "Obesity-Associated Autoantibody Production Requires AIM to Retain the Immunoglobulin M Immune Complex on Follicular Dendritic Cell", Cell Reports, Apr. 25, 2013, pp. 1187-1189; cited in the Specification.
Uramatsu, T. et al., "Involvement of Apoptosis Inhibitor of Macrophage in a Rat Hypertension Model with Nephrosclerosis: Possible Mechanisms of Action of Olmesartan and Azelnidipine", Biol. Pharm. Bull., 2013, pp. 1271-1277; cited in the Specification.
Miyazaki, T., "Diagnostic Significance and Clinical Application of Apoptosis Inhibitor of Macrophage (AIM) on Various Modern Diseases", Japanese Society of Veterinary Clinical Pathology 2014 Conference, Abstracts, with English translation; cited in the Specification.
Kitada, K. et al. "Apoptosis Inhibitor of Macrophage (AIM) enhances exclusion of renal tubular necrosis and includes repair and recovery of renal disorder", The Japanese Journal of Nephrology, 2014, vol. 56, No. 3, p. 321, with English translation; cited in the Specification and ISR.

(Continued)

*Primary Examiner* — Gary Counts
(74) *Attorney, Agent, or Firm* — Westerman, Hattori, Daniels & Adrian, LLP

(57) ABSTRACT

A method for detecting renal disease or a method for assisting diagnosis of renal disease that is superior in sensitivity and specificity, as well as a kit that can be used therefor is provided. The present invention provides a method for detecting renal disease or a method for assisting diagnosis of renal disease comprising a step of detecting or quantifying free AIM in a biological sample derived from a test subject, as well as a kit for examining or assisting diagnosis of renal disease comprising an antibody that binds to free AIM.

10 Claims, 3 Drawing Sheets

(56) References Cited

OTHER PUBLICATIONS

Arai, S. et al., "Apoptosis inhibitor of macrophage protein enhances intraluminal debris clearance and ameliorates acute kidney injury in mice", Nature Medicine, 2016, vol. 22, No. 2, pp. 183-193; cited in ISR.

* cited by examiner

[Figure 1]
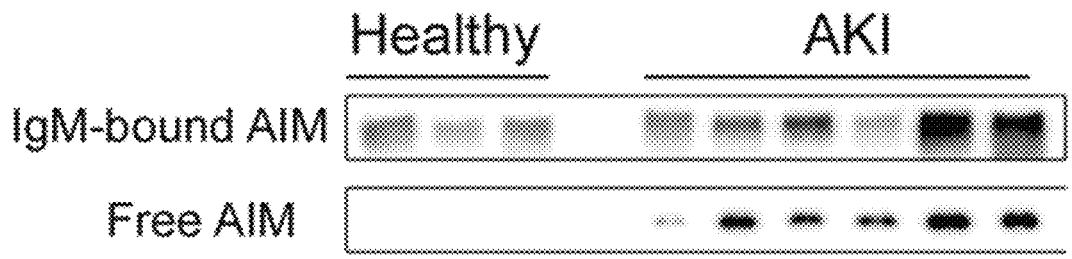
[Figure 2]
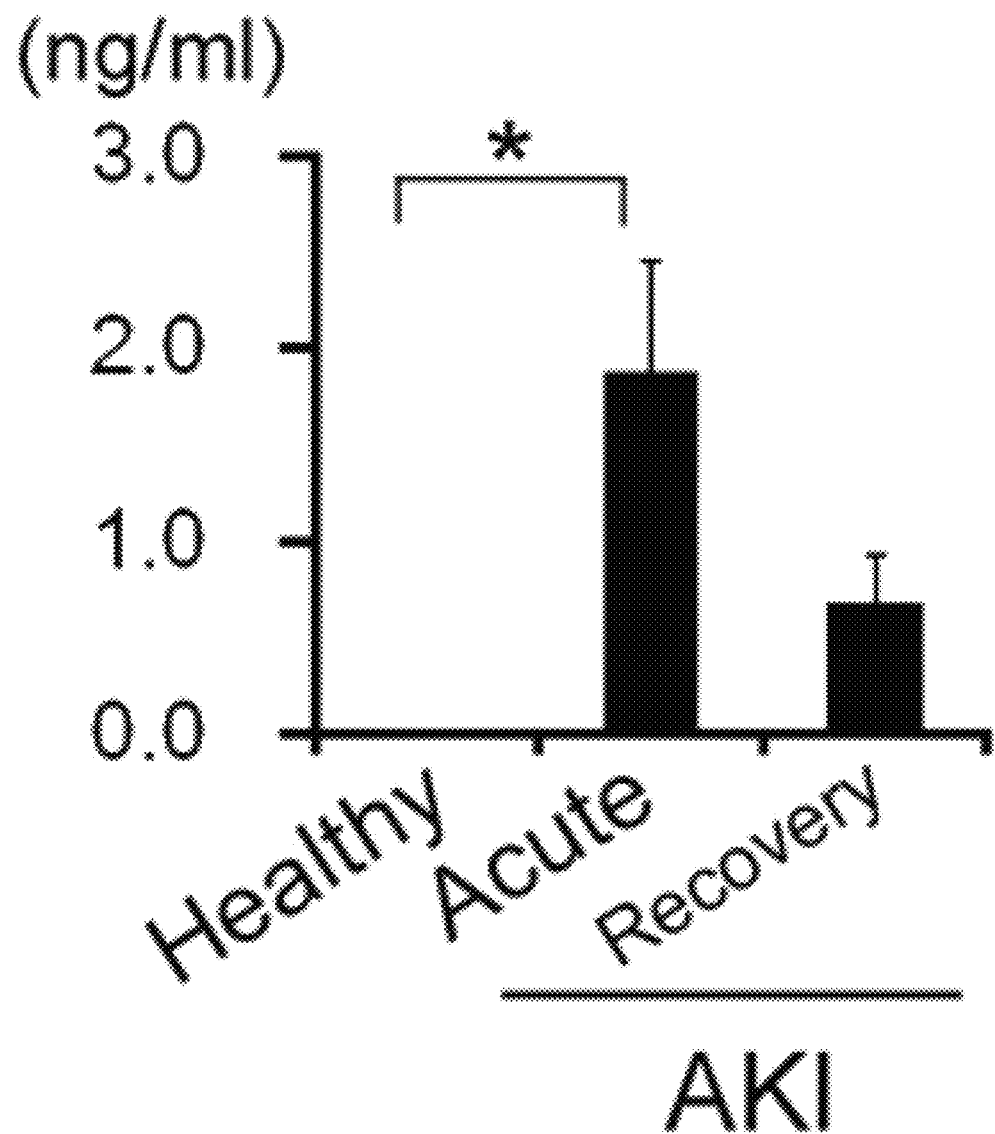

[Figure 3]
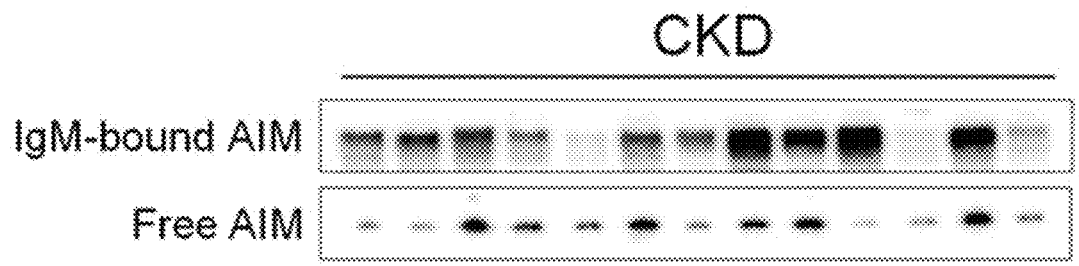

[Figure 4]
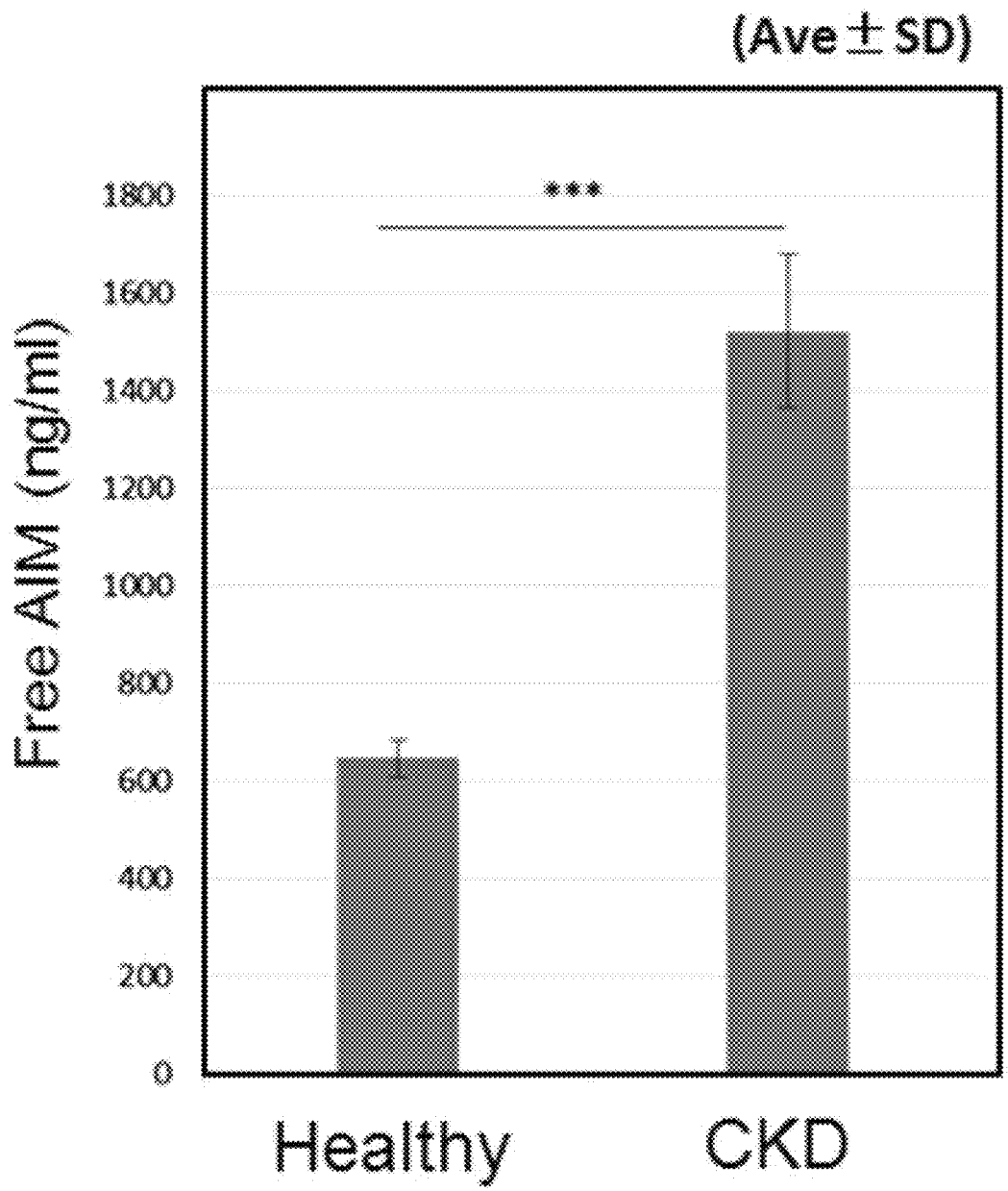

METHOD FOR EXAMINING RENAL DISEASE

TECHNICAL FIELD

The present invention typically relates to a method for examining renal disease or a method for assisting diagnosis of renal disease. Specifically, the present invention relates to a method for examining renal disease or a method for assisting diagnosis of renal disease, comprising detecting free AIM in a biological sample of a test subject. The present invention further relates to a kit for examining or assisting diagnosis of renal disease.

BACKGROUND ART

AIM (apoptosis inhibitor of macrophage; also referred to as CD5L, api6, or Spα) is a secretory protein having a molecular weight of approximately 50 kDa that is specifically produced by tissue macrophage (Non-Patent Literature 1). AIM has a structure of tandemly connected three scavenger receptor cysteine-rich (SRCR) domains which are specific sequences containing a large number of cysteine residues, and it is thought to have a compact spherical conformation due to each cysteine residue being bound to one another by disulfide bonds within each domain.

AIM is an adhesive protein, and various molecules have been reported as binding partners thereof. For example, it is known to recognize the pathogen-associated molecular pattern (PAMPs) of bacteria and fungus such as lipoteichoic acid (LTA) and lipopolysaccharide (LPS), and have the ability to aggregate bacteria (Non-Patent Literature 2). There are also many cells in the body that bind AIM on their surface or incorporate it into the cell, and it has been reported that AIM is incorporated into macrophage itself which is the producer cell, or that it is incorporated by endocytosis via scavenger receptor CD36 in fat cells to induce fat degradation (Non-Patent Literature 3).

It has also been long known that AIM binds to IgM in blood (Non-Patent Literature 4). In recent years, it has been reported that binding to IgM is closely involved in order for AIMs to be not excreted into urine and to exist stably in blood, and that nearly all AIMs are bound to IgM in the blood and they are rarely present as monomers (Non-Patent Literatures 5 and 6).

There have been several reports thus far on the relationship between AIM and renal disease. For example, Patent Literature 1 discloses a method for diagnosing or examining AIM-associated disease comprising measuring the AIM concentration in a sample collected from a test subject, wherein renal disease is listed as a said associated disease.

Non-Patent Literature 7 describes the correlation between AIM expression in renal tissue macrophage of a SHRsp rat and the number of macrophage invasion, suggesting that expression of AIM is key to the progression of nephrosclerosis.

Non-Patent Literature 8 describes that insufficient blood AIM significantly increases the risk of progressing from a renal disorder event to a chronic renal failure.

Non-Patent Literature 9 describes that in the process of investigating the role of AIM in the onset and progress of renal disorder, in a unilateral urinary obstruction model or a renal ischemia reperfusion model, renal tissue disorder accompanied by tubular necrosis is significantly enhanced in an AIM-deficient mouse compared to a wildtype mouse.

However, there have been no reports thus far regarding the relationship between AIM that is present in free form not bound to other binding partners and renal disease.

PRIOR ART

Patent Literature

[Patent Literature 1] International Publication WO 2011/145725 A1

Non-Patent Literature

[Non-Patent Literature 1] Miyazaki, J Exp Med 189:413-422, 1999
[Non-Patent Literature 2] Sarrias M R et al: A role for human Sp alpha as a pattern recognition receptor. J Biol Chem 280:35391-35398, 2005
[Non-Patent Literature 3] Kurokawa J. et al: Macrophage-derived AIM is endocytosed into adipocytes and decreases lipid Droplets via inhibition of fatty acid synthase activity. Cell Metab 11:479-492, 2010
[Non-Patent Literature 4] Tissot J D et al: IgM are associated to Sp alpha (CD5 antigen-like). Electrophoresis 23:1203-1206, 2002.
[Non-Patent Literature 5] Miyazaki et al.: "Latest Knowledge on Macrophage-derived Protein AIM—Their Diverse functions and Association with Lifestyle-related Diseases-", Nippon Rinsho, Vol. 71, No. 9 (2013-9), pages 1681-1689
[Non-Patent Literature 6] Miyazaki et al., Obesity-Associated Autoantibody Production Requires AIM to Retain the Immunoglobulin M Immune Complex on Follicular Dendritic Cells, Cell Reports 3, 1187-1198, Apr. 25, 2013
[Non-Patent Literature 7] Involvement of Apoptosis Inhibitor of Macrophages in a Rat Hypertension Model with Nephrosclerosis: Possible Mechanisms of Action of Olmesartan and Azelnidipine: Biol. Pharm. Bull. 36 (8) 1271-1277 (2013) 1271
[Non-Patent Literature 8] Japanese Society of Veterinary Clinical Pathology 2014 Conference, Abstracts
[Non-Patent Literature 9] The Japanese Journal of Nephrology, 2014, Vol. 56, No. 3, page 321

SUMMARY OF THE INVENTION

Problems to be Solved by the Invention

The object of the present invention is to provide a method for detecting renal disease or a method for assisting diagnosis of renal disease that is superior in sensitivity and specificity, as well as a kit that can be used therefor.

Means for Solving the Problems

As a result of repeated extensive investigation by the present inventors to solve the above problem, it was found that free AIM is significantly increased in a biological sample of a renal disease test subject. As it was thought that free AIM could normally be barely confirmed in blood, it was surprising that, among other things, significant increase of free AIM in the blood of renal disease test subject was confirmed.

The present invention is based on the above knowledge, and encompasses the following characteristics.

Namely, in one embodiment, the present invention relates to a method for examining renal disease comprising a step of detecting or quantifying free AIM in a biological sample derived from a test subject. In another aspect, the present invention can be a method for assisting diagnosis of renal disease comprising a step of detecting or quantifying free AIM in a biological sample derived from a test subject. In yet another aspect, the present invention can be a method for detecting or quantifying free AIM in a biological sample derived from a test subject for examining renal disease.

In the method of the present invention, said biological sample can be a body fluid. Moreover, in one embodiment of the method of the present invention, said body fluid can be one selected from the group consisting of serum, blood plasma, whole blood, and urine.

In one embodiment, the method of the present invention is characterized in that said detection or quantification is one by immunoassay. For example, in the method of the present invention, said detection or quantification can be one that is performed by contacting a biological sample with an antibody that binds to free AIM. In one embodiment of the method of the present invention, said antibody that binds to free AIM is an antibody that specifically binds to free AIM. Moreover, in one embodiment of the present invention, said detection or quantification can be measurement by ELISA.

In one embodiment, the method of the present invention is characterized in that said detection or quantification is performed without exposing the blood sample selected from serum, blood plasma, or whole blood to a protein denaturing condition and without exposing to a reductive condition.

The present invention also relates to a kit for examining or assisting diagnosis of renal disease comprising an antibody that binds to free AIM. In one embodiment of the kit of the present invention, said antibody that binds to free AIM is an antibody that specifically binds to free AIM.

In the present invention, said renal disease can be an acute kidney injury or a chronic kidney disease. In one embodiment, said chronic kidney disease can be chronic nephritis, chronic renal failure, nephrotic syndrome, diabetic nephropathy, nephrosclerosis, IgA nephropathy, hypertensive nephropathy, nephropathy associated with collagen disease, or IgM nephropathy.

Effects of the Invention

According to the present invention, there is provided a method for detecting renal disease or a method for assisting diagnosis of renal disease that is superior in sensitivity and specificity, as well as a kit that can be used therefor.

BRIEF DESCRIPTION OF THE DRAWINGS

FIG. 1 is an electropherogram showing the result of detecting free AIM and IgM-bound AIM with an anti-AIM antibody in the serum of healthy individuals and acute kidney injury (AKI) patients.

FIG. 2 is the result of ELISA analysis detecting the concentration of free AIM in urine with human AIM monoclonal antibody in each of five healthy individual cases, five AKI patient cases (Acute), and five recovered-from-AKI cases (Recovery).

FIG. 3 is an electropherogram showing the result of detecting free AIM and IgM-bound AIM with an anti-AIM antibody in chronic kidney disease (CKD) patient serums.

FIG. 4 is the result of detecting free AIM with Human AIM ELISA kit (CY-8080; from CircuLex) in the serum of healthy individuals and chronic kidney disease (CKD) patients.

DESCRIPTION OF EMBODIMENTS

The embodiments of the present invention will now be specifically described.

The method for examining renal disease according to the present invention comprises a step of detecting or quantifying free AIM in a biological sample derived from a test subject. As described above, AIM is a secretory protein having a molecular weight of approximately 50 kDa that is specifically produced by tissue macrophage, and is known to be expressed in humans and many mammals other than humans as well as birds. It is also known that in order for AIM to exist stably in blood without being excreted into urine, nearly all AIMs form a complex with IgM and they are rarely present as monomers (Non-Patent Literatures 5 and 6). It has further been reported that insufficient AIM in blood is associated with the risk of progressing to a chronic renal failure (Non-Patent Literature 8). On the other hand, in spite of this knowledge, it has now been found that free AIM in biological samples including blood samples is significantly increased in acute and chronic kidney disease test subjects. Accordingly, by detecting or quantifying free AIM in a biological sample derived from a test subject, renal disease can be detected with good detection sensitivity and specificity in the aforementioned test subject. "Free AIM" as used herein refers to monomer AIM in a biological sample that has not formed a complex with other binding partners of AIM, in particular IgM.

In another aspect, the present invention relates to a method for assisting diagnosis of renal disease comprising a step of detecting or quantifying free AIM in a biological sample derived from a test subject.

"Examining renal disease" or "assisting diagnosis of renal disease" as used herein means inspecting a sample collected from a test subject in order to obtain information necessary for diagnosis. Accordingly, the method of the present invention may be carried out at e.g. an examination company.

In yet another aspect, the present invention relates to a method for detecting or quantifying free AIM in a biological sample derived from a test subject for examining renal disease.

In the present invention, the test subject is not particularly limited but includes e.g. a test subject having a risk of developing or suspected of having developed renal disease. The test subject also includes a test subject who has already developed renal disease, in which case the present invention can be carried out with the objective to determine the prognosis of such test subject or to determine the effect of a particular renal disease therapy. The test subject typically refers to a human, but may also include other animals including e.g. other primates, rodents, a dog, a cat, a horse, a sheep, a pig, and the like.

In the present invention, a renal disease includes both acute and chronic kidney diseases. A chronic kidney disease includes, but is not limited to, e.g. chronic nephritis, chronic renal failure, nephrotic syndrome, diabetic nephropathy, nephrosclerosis, IgA nephropathy, hypertensive nephropathy, nephropathy associated with collagen disease, IgM nephropathy, and the like.

In the present invention, a biological sample derived from a test subject is not particularly limited as long as it can be collected from a test subject, and can be e.g. tissue or body fluid. A tissue includes, non-limitingly, ovary, uterus, breast, thyroid, brain, esophagus, tongue, lung, pancreas, stomach, small intestine, duodenum, large intestine, bladder, kidney, liver, prostate, gallbladder, pharynx, muscle, bone and skin, and the like, but is not limited thereto. A body fluid includes, non-limitingly, blood such as serum, blood plasma, or whole blood, lymph, tissue fluid, body cavity fluid, digestive juice, nasal discharge, urine, and the like, but it not limited thereto. In terms of ease of acquirement and treatment, it is preferred to employ blood or urine as the biological sample. Moreover, said body fluid can be a body fluid itself that is collected from a test subject, or it may be those subjected to treatments such as dilution or concentration ordinarily performed on collected body fluids. Note that the person who collects and prepares the biological sample derived from a test subject employed in the present invention may be the same or different from the person who performs the steps of the present invention. Moreover, the biological sample derived from a test subject employed in the present invention may be collected or prepared at the time of carrying out the present invention, or collected or prepared in advance and stored.

The method for detecting or quantifying free AIM is not particularly restricted as long as it is a method that can detect and discriminate between free AIM and AIM that has formed a complex with other binding partners (such as IgM) (hereinafter also referred to as complex AIM), and an ordinarily employed protein detection method can be applied. It is also preferred that such a protein detection method is a method that can quantify or semi-quantitatively measure free AIM. Such a method can include, but is not limited to, a method employing an antibody that binds to free AIM, ion exchange chromatography, mass spectrometry, and the like.

In the present invention, the device employed for detecting free AIM is not particularly restricted, and can be appropriately selected depending on the method for detecting or measuring free AIM. This can include, specifically, e.g. an HPLC instrument, a mass spectrometry instrument, an electrophoresis instrument (such as a capillary electrophoresis device), an automatic or semi-automatic enzyme immunoassay instrument, a cell washer, an automatic or semi-automatic chemiluminescent immunoassay instrument, a luminescence measuring device, an automatic or semi-automatic electrochemiluminescent immunoassay instrument, an optical measuring device, a plate reader, a CCD camera, an automatic or semi-automatic fluorescent immunoassay instrument, a fluorescence measuring device, an automatic or semi-automatic radioimmunoassay instrument, a liquid scintillation counter, a Coulter counter, a surface plasmon measuring device, a blotting device, a densitometer, and the like.

In the present invention, in terms of detection sensitivity, specificity, and convenience, it is preferred to use a method that employs an antibody that binds to free AIM (also referred to herein as an "anti-free AIM antibody"), e.g. an immunoassay that employs an antibody that binds to free AIM. The anti-free AIM antibody is not particularly limited as long as it is an antibody that can recognize and bind AIM.

For the anti-free AIM antibody, both monoclonal and polyclonal antibodies can be produced according to a well-known method. A monoclonal antibody can for example be obtained by isolating antibody-producing cells from a non-human mammal immunized with a free AIM or free AIM fragment, fusing them with myeloma cells etc. to produce hybridomas, and purifying the antibody produced by this hybridoma. Moreover, a polyclonal antibody can be obtained from the serum of an animal immunized with a free AIM or free AIM fragment.

A free AIM fragment is a partial peptide of free AIM, and an anti-free AIM fragment antibody recognizes free AIM. Moreover, the immunogen includes, but is not limited to, e.g. a free AIM or free AIM fragment of primates such as a human or a monkey, rodents such as a rat or a mouse, a dog, a cat, a horse, a sheep, a pig, and the like.

An "antibody" as used herein refers to a full length immunoglobulin molecule that exists in nature or is produced by a genetic recombination technology, or an immunologically active fragment of an immunoglobulin molecule such as an antibody fragment. Unless particularly noted, the antibody of the present invention includes any type, class, or subclass, e.g. includes IgG, IgE, IgM, IgD, IgA, IgY, $IgG_1$, $IgG_2$, $IgG_3$, $IgG_4$, $IgA_1$, $IgA_2$, and the like. These antibodies can be produced with a conventional technology, and may be a polyclonal antibody or a monoclonal antibody. An antibody fragment includes $F(ab')_2$, $F(ab)_2$, Fab', Fab, Fv, scFv, and the like. An antibody fragment can be produced by e.g. genetic recombination technology employing an encoding nucleic acid, or it can also be produced by cleaving a full length antibody with an enzyme. In the present invention, it is preferred that the anti-free AIM antibody is a monoclonal antibody.

In the present invention, examples of an anti-free AIM antibody can include e.g. AIM-CL-6 (Accession No: NITE BP-1092) and AIM-CL-7 (Accession No: NITE BP-1093) deposited at the National Institute of Technology and Evaluation Patent Microorganisms Depository.

It is preferred that the anti-free AIM antibody used in the present invention is an antibody that specifically binds to free AIM. "Specific binding" refers to a binding that is different in measurement from a non-specific interaction, and further herein to an antibody that has higher binding affinity to free AIM than to AIM that has formed a complex with IgM. In one aspect of the present invention, "specific binding" may be shown by e.g. an antibody with a Kd of at least approximately $10^{-4}$ M, or at least approximately $10^5$ M, or at least approximately $10^{-6}$ M, or at least approximately $10^{-7}$ M, or at least approximately $10^{-8}$ M, or at least approximately $10^{-9}$ M, or at least approximately $10^{-10}$ M, or at least approximately $10^{-11}$ M, or at least approximately $10^{-12}$ M or more against a free AIM. In another aspect, "specific binding" means binding to free AIM without substantial binding to polypeptides other than free AIM, including AIM that has formed a complex with IgM.

A method commonly used by those skilled in the art can be employed as the immunoassay in the present invention, although a method or a condition where free AIM and complex AIM are detected or quantified with discrimination should be selected. For example, in the method of the present invention, when a biological sample other than urine, for example a blood sample selected from serum, blood plasma, or whole blood is employed, it is preferred to perform fractionation of the biological sample based on molecular weight as necessary upon detection or quantification with an anti-free AIM antibody so that free AIM and complex AIM are detected with discrimination. It is also preferred to perform detection or quantification with an anti-free AIM antibody after separating free AIM from complex AIM. Moreover, in the method of the present invention, care should be taken so that said biological sample is not exposed to a protein denaturing condition or a reductive condition in which the bound state of the AIM that has formed a complex with IgM gets dissolved. Such a protein denaturing condition or a reductive condition is well-known to those skilled in the art as a method or condition that destroys protein quaternary structure.

An immunoassay employs a detectably labeled anti-free AIM antibody, or an antibody against a detectably labeled anti-free AIM antibody (secondary antibody). Depending on the method of labeling the antibody, they are classified into enzyme immunoassay (EIA or ELISA), radioimmunoassay (RIA), fluorescent immunoassay (FIA), fluorescence polarization immunoassay (FPIA), chemiluminescent immunoassay (CLIA), electrochemiluminescent immunoassay (ECLIA), and the like, any of which can be employed in the method of the present invention.

An antibody labeled with an enzyme such as peroxidase and alkaline phosphatase is employed in the ELISA method, with a radioactive material such as $^{125}$I, $^{131}$I, $^{35}$S, and $^{3}$H in the RIA method, with a fluorescent substance such as fluorescein isothiocyanate, rhodamine, dansyl chloride, phycoerythrin, tetramethylrhodamine isothiocyanate, and near-infrared fluorescence material in the FPIA method, and with a luminescent substance such as luciferase, luciferin, and aequorin in the CLIA method. In addition, an antibody labeled with a nanoparticle such as gold colloid and quantum dot can also be detected.

In an immunoassay, anti-free AIM antibody can also be labeled with biotin, and bound to avidin or streptavidin labeled with e.g. an enzyme to detect and measure free AIM.

Among immunoassays, the ELISA method which employs an enzyme label is preferred in that it can conveniently and rapidly measure a target.

In the ELISA method, the sandwich method can for example be employed. The anti-free AIM antibody is fixed onto a solid phase carrier, an appropriately treated biological sample is added and allowed to react, and then an anti-free AIM antibody that recognizes another epitope labeled with an enzyme is further added and allowed to react.

After washing, the mixture is reacted with an enzyme substrate for color development, and absorbance can be measured to determine the concentration of free AIM. Moreover, after allowing the anti-free AIM antibody fixed onto the solid phase carrier and the free AIM in the biological sample to react, an unlabeled free AIM antibody (primary antibody) is added, and an antibody against this unlabeled antibody (secondary antibody) may be labeled with an enzyme and further added.

When the enzyme is a peroxidase, 3,3'-diaminobenzidine (DAB), 3,3'5,5'-tetramethylbenzidine (TMB), o-phenylenediamine (OPD), and the like can be employed as the enzyme substrate, and when it is an alkaline phosphatase, p-nitropheny phosphate (NPP) and the like can be employed.

In the above immunoassay, the aggregation method is also preferred as a method that can conveniently detect a trace amount of protein. An aggregation method includes e.g. the latex aggregation method having an antibody bound to a latex particle.

When a latex particle is bound to an anti-free AIM antibody and mixed with a biological sample, the antibody-bound latex particles aggregate if free AIM is present. The aggregated mass is then quantified by irradiating near-infrared light on the sample and measuring absorbance (turbidimetry) or scattered light (nephelometry) to determine the concentration of antigen.

In the present invention, a kit that can specifically detect free AIM can be employed for detecting or quantifying free AIM. The aforementioned kit can include e.g. a commercially available kit, and can also be implemented by employing it according to the instruction of the aforementioned kit. Such a kit can include, but is not limited to, Human AIM ELISA kit (CY-8080; from CircuLex) and the like.

The method of the present invention can further comprise a step of determining renal disease based on the amount of free AIM in a biological sample from said test subject. The amount of free AIM in the present invention is not particularly limited, as long as it is the concentration of said free AIM contained in a biological sample from said test subject, or a quantitative value or a semi-quantitative value corresponding thereto. Examples of the amount of free AIM in the present invention can include the measurement value of directly measuring the amount of said free AIM detected, the measurement value of indirectly measuring the amount of said free AIM detected via detection of a label, and the like.

In the determination step in the method of the present invention, by comparing the amount of free AIM in a biological sample from a test subject with e.g. the amount of free AIM in a biological sample of a control healthy individual as the reference value, renal disease can be determined if the amount of free AIM in a biological sample from said test subject is larger.

The control healthy individual means an individual who is proven in advance to not have developed renal disease. Moreover, the amount of free AIM is larger refers to that the amount of free AIM from the test subject is larger than the reference value (cutoff value) set to discriminate a healthy individual from a renal disease patient.

Said reference value can be set for example by subjecting the amount of free AIM in a biological sample of a renal disease patient and the amount of free AIM in a biological sample of a control group of healthy individuals to ROC analysis and the like. ROC analysis is for example an analysis method that can evaluate the detecting and diagnosing ability of a method for examining an illness, such as an analysis method that was described in The Japan Society for Clinical Laboratory Automation Journal "Evaluation Manual for Diagnostic Utility of Clinical Examination", Ver. 1.3 (2004.9.1), Vol. 29 Suppl. 1 (Whole Number 154) (Published Sep. 1, 2004).

The reference value can also be set as e.g. the sum of the average value of the detection levels of healthy individuals and two- or three-folds of the standard deviation value, and can further be appropriately set as a value that fulfills sensitivity (detection rate) and specificity (how low the rate of false positives is) in a balanced manner.

In another aspect, the present invention relates to a kit for examining or assisting diagnosis of renal disease. In one aspect of the present invention, the kit according to the present invention is a kit for performing the above-described method for examining renal disease according to the present invention, and comprises an anti-free AIM antibody. In one embodiment of the kit of the present invention, an anti-free AIM antibody is an antibody that specifically binds to free AIM.

The aforementioned kit for examining or assisting diagnosis comprises a reagent and a device necessary for measuring the concentration of free AIM in the biological sample by an immunoassay that utilizes the antigen antibody reaction between free AIM and an anti-free AIM antibody.

In one aspect, the kit of the present invention is for measuring the concentration of free AIM by a sandwich ELISA method, and comprises a microtiter plate; an anti-free AIM antibody for capturing; an anti-free AIM antibody labeled with an alkaline phosphatase or a peroxidase; and an alkaline phosphatase substrate (such as NPP) or a peroxidase substrate (such as DAB, TMB, and microtiter plate OPD).

The capturing antibody and the labeled antibody recognize different epitopes.

In such a kit, the capturing antibody is first fixed onto a microtiter plate, an appropriately treated and diluted biological sample is added thereto and then incubated, and the sample is removed and washed. Subsequently, the labeled antibody is added and then incubated, and the substrate is added for color development. By measuring the color development with e.g. a microtiter plate reader, the concentration of free AIM can be determined.

In another aspect, the kit of the present invention is for measuring the concentration of free AIM by the sandwich ELISA method that uses a secondary antibody, and comprises a microtiter plate; an anti-free AIM antibody for capturing; an anti-free AIM antibody as the primary antibody; an antibody against an anti-free AIM antibody labeled with an alkaline phosphatase or a peroxidase as the secondary antibody; and an alkaline phosphatase (such as NPP) or a peroxidase substrate (such as DAB, TMB, and OPD).

The capturing antibody and the primary antibody recognize different epitopes.

In such a kit, the capturing antibody is first fixed onto a microtiter plate, an appropriately treated and diluted biological sample is added thereto and then incubated, and the sample is removed and washed. Subsequently, the primary antibody is added followed by incubation and washing, an enzyme-labeled secondary antibody is further added and incubated, and then the substrate is added for color development. By measuring the color development with e.g. a microtiter plate reader, the concentration of free AIM can be determined. By employing a secondary antibody, the reaction is amplified and detection sensitivity can be increased.

It is also preferred that the kit of the present invention further comprises the necessary buffer, enzyme reaction quenching solution, a microplate, and the like.

The labeled antibody is not limited to an enzyme-labeled antibody, and may be an antibody labeled with a radioactive material (such as $^{125}$I, $^{131}$I, $^{35}$S, and $^{3}$H), a fluorescent substance (such as fluorescein isothiocyanate, rhodamine, dansyl chloride, phycoerythrin, tetramethylrhodamine isothiocyanate, and near-infrared fluorescence material), a luminescent substance (such as luciferase, luciferin, and aequorin), a nanoparticle (gold colloid and quantum dot), and the like. It is also possible to employ a biotinylated antibody as the labeled antibody and add a labeled avidin or streptavidin to the kit.

Yet another aspect of the diagnostic kit of the present invention includes those for measuring the concentration of free AIM by the latex aggregation method. This kit comprises anti-free AIM antibody-sensitized latex, wherein the biological sample and the anti-free AIM antibody are mixed and the agglomerate is quantified by an optical method. It is also preferred that the kit comprises an aggregation reaction plate for visualizing the aggregation reaction.

Yet another aspect of the diagnostic kit of the present invention includes those for measuring the concentration of free AIM by the electrochemiluminescence method. This kit comprises a carrier supporting an anti-free AIM antibody, wherein an appropriately treated and diluted biological sample is added and then incubated, and the sample is removed and washed. Subsequently, an electrochemiluminescent substance (such as ruthenium)-labeled antibody is added and then incubated, and an electrical energy is applied on the electrode to allow luminescence. This amount of luminescence is measured to quantify the concentration of free AIM.

The present invention will now be more specifically described with Examples. The present invention is not to be limited in any way by the Examples shown below.

EXAMPLES

Example 1: Preparation of Mouse Anti-Human AIM Monoclonal Antibody

Animal Sensitization

As the antigen, full length human rAIM (2 mg/ml) was mixed with an equal amount of TiterMax Gold (G-1, Funakoshi) to prepare an emulsion. Two 8 week old female Balb/c mice (from Charles River) were employed as immune animals, and 50 μL was administered to the posterior plantar region. A similar administration was performed after 2 weeks, and 50 μg of the antigen solution was administered to the posterior plantar region after another 2 weeks or more in order to prepare for cell fusion 3 days later.

Myeloma Cell

Mouse P3U1 was employed for the myeloma cell, and a medium which was RPMI1640 (11875-119 GIBCO) supplemented with glutamine and pyruvic acid and having FBS (S1560 from BWT) added to be 10% was employed as the proliferation culture. As antibiotics, penicillin and streptomycin were added at appropriate amounts.

Cell Fusion

From a mouse from which cardiac blood was collected under anesthesia, popliteal lymph nodes were aseptically resected, placed on a beaker with a #200 mesh, and a cell suspension was prepared by thrusting with a silicon stick. The cells were subjected to centrifugation wash two times in RPMI1640, and then the number of cells was counted. Myeloma cells in the logarithmic growth phase state were collected by centrifugation and washed, after which the ratio of lymphocytes to myeloma cells was adjusted to be 5 to 1, and mixed centrifugation was performed. Cell fusion was performed with PEG1500 (783641, Roche). In other words, cell pellets were allowed to react with 1 mL of PEG solution over 3 minutes, this was serially diluted and washed by centrifugation, the medium was added and 200 μL each was placed in fifteen 96-well plates, and subjected to 1 week of culture. As the medium, a myeloma cell medium supplemented with HAT Supplement (21060-017, GIBCO) and FBS concentration adjusted to 15% was employed.

Collection of Mouse Peritoneal Fluid

Fused cells stored in a frozen state were thawed, proliferation culture was performed, then 1×10$^7$ cells were administered to the peritoneal cavity of a nude mouse (BALB/cAJcl-nu/nu, CLEA Japan) having 0.5 ml of pristane (42-002, Cosmo Bio) intraperitoneally administrated 1 week or more beforehand, and 4-12 ml of peritoneal fluid was obtained after about 2 weeks later. Solids were removed by centrifugation treatment and then this was stored in a frozen state.

Example 2: Expression of Free AIM in Serum in Acute Kidney Injury Patient Serum AIM in the serum of 3 healthy individual cases and 6 acute kidney injury (AKI) patient cases were investigated with Western blot employing anti-AIM antibody. The serum was subjected to SDS-polyacrylamide gel electrophoresis under a nonreductive condition, the protein was transferred onto a PVDF membrane (Immobilon, from Millipore), and primary antibody reaction was performed with the mouse anti-human AIM monoclonal antibody prepared in Example 1 at 4° C. overnight. HRP-bound anti-mouse IgG antibody was employed as the secondary antibody, Luminata Forte Western HRP Substrate (from Millipore) was employed as the detection reagent, and signal detection was carried out with Image Quant LAS 4000 (GE Healthcare).

Under a nonreductive condition, AIM bound to IgM having a molecular weight >600 kDa was detected in the healthy individual serum, but free AIM band of molecular weight <40 kDa was detected in addition to the IgM-bound AIM band in the 6 AKI patient serums (FIG. 1).

Example 3: Increase in Free AIM in Acute Kidney Injury Patient Urine

Using ELISA for quantifying AIM, the concentration of free AIM in urine of healthy individuals and AKI patients was measured. In AIM ELISA, the mouse anti-human AIM monoclonal antibody prepared in Example 1 was solid-phased onto a plate, and patient urine was added. After washing, HRP-labeled mouse anti-human AIM monoclonal antibody was allowed to react, and color was developed by an HRP substrate. Since only free AIM exists in the urine, the AIM in urine detected by this ELISA is free AIM.

The concentration of free AIM in urine of 5 healthy individual examples, 5 AKI patient examples (Acute), and 5 recovered-from-AKI examples (Recovery) were measured. Man-Whittney U test was employed for statistical analysis. As a result, the concentration of free AIM in urine significantly higher in AKI patients compared to healthy individuals ($p<0.001$). It was also shown that the concentration of free AIM in urine is reduced with recovery from AKI (FIG. 2).

Example 4: Expression of Free AIM in Serum in Chronic Kidney Disease Patient Serum AIM in the serum of 3 healthy individual cases and 13 chronic kidney disease (CKD) patient cases were investigated with Western blot employing anti-AIM antibody by the method described in Example 2. In the CKD patient serum, free AIM band of molecular weight <40 kDa was detected in addition to the IgM-bound AIM band of molecular weight >600 kDa (FIG. 3). CKD patients in the present method included patients of chronic nephritis (chronic glomerulonephritis), diabetic nephropathy, IgA nephropathy, and nephrosclerosis.

Example 5: Concentration of Free AIM in CKD Patient Serum

Using Human AIM ELISA kit (CircuLex, CY-8080) that quantifies free AIM, the concentration of free AIM in the serum of 20 healthy individual cases and 15 CKD patient cases were measured. Measurement was carried out according to the instruction of the kit. Man-Whittney U test was employed for statistical analysis. As a result, the concentration of free AIM was significantly higher in CKD patients compared to healthy individuals (FIG. 4) ($p<0.001$).

INDUSTRIAL APPLICABILITY

By employing the method and/or the examination or diagnosis assisting kit of the present invention, renal disease can be examined with superior sensitivity and specificity.

The invention claimed is:

1. A method for examining renal disease comprising:
   detecting or quantifying free apoptosis inhibitor of macrophage (AIM) in a biological sample derived from a test subject,
   wherein the presence of a greater amount of the free AIM in the test subject than an amount of the free AIM in a subject not having the renal disease indicates that the test subject has the renal disease,
   wherein said biological sample is selected from the group consisting of serum, blood plasma, and whole blood,
   wherein said renal disease is an acute kidney injury or a chronic kidney disease, and
   wherein the test subject is a human subject.

2. A method for assisting diagnosis of renal disease comprising:
   detecting or quantifying free apoptosis inhibitor of macrophage (AIM) in a biological sample derived from a test subject,
   wherein the presence of a greater amount of the free AIM in the test subject than an amount of the free AIM in a subject not having the renal disease indicates that the test subject has the renal disease,
   wherein said biological sample is selected from the group consisting of serum, blood plasma, and whole blood,
   wherein said renal disease is an acute kidney injury or a chronic kidney disease, and
   wherein the test subject is a human subject.

3. A method for detecting or quantifying free apoptosis inhibitor of macrophage (AIM) in a biological sample of a human test subject for examining renal disease, comprising:
   subjecting the biological sample to detection of free AIM while discriminating between free AIM and AIM that has formed a complex with another binding partner,
   wherein said biological sample is selected from the group consisting of serum, blood plasma, and whole blood, and
   wherein said renal disease is an acute kidney injury or a chronic kidney disease.

4. The method according to claim 3, wherein said chronic kidney disease is chronic nephritis, chronic renal failure, nephrotic syndrome, diabetic nephropathy, nephrosclerosis, IgA nephropathy, hypertensive nephropathy, nephropathy associated with collagen disease, or IgM nephropathy.

5. The method according to claim 1, wherein said detection or quantification is by immunoassay.

6. The method according to claim 5, wherein said detection or quantification is performed by contacting a biological sample with an antibody that binds to free AIM.

7. The method according to claim 6, wherein said detection or quantification is performed by an antibody that specifically binds to free AIM.

8. The method according to claim 6, wherein said detection or quantification is measurement by ELISA.

9. The method according to claim 5, wherein said detection or quantification is performed without exposing serum, blood plasma, or whole blood to a protein denaturing condition and without exposing the serum, blood plasma, or whole blood to a reductive condition.

10. The method according to claim 3, wherein said detection or quantification is performed after separating free AIM and complexed AIM.

* * * * *